United States Patent
Wallick

(10) Patent No.: US 8,998,987 B2
(45) Date of Patent: Apr. 7, 2015

(54) ORTHOPEDIC IMPLANT WITH POROUS POLYMER BONE CONTACTING SURFACE

(75) Inventor: Michael Wallick, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 212 days.

(21) Appl. No.: 13/884,171

(22) PCT Filed: Nov. 11, 2011

(86) PCT No.: PCT/US2011/060379
§ 371 (c)(1),
(2), (4) Date: Sep. 16, 2013

(87) PCT Pub. No.: WO2012/065068
PCT Pub. Date: May 18, 2012

(65) Prior Publication Data
US 2013/0345827 A1   Dec. 26, 2013

Related U.S. Application Data

(60) Provisional application No. 61/412,510, filed on Nov. 11, 2010.

(51) Int. Cl.
*A61F 2/28*   (2006.01)
*A61F 2/36*   (2006.01)
*A61F 2/30*   (2006.01)

(52) U.S. Cl.
CPC ... *A61F 2/28* (2013.01); *A61F 2/36* (2013.01); *A61F 2002/30011* (2013.01); *A61F 2002/30014* (2013.01); *A61F 2002/30065* (2013.01); *A61F 2002/3092* (2013.01); *A61F 2002/30971* (2013.01); *A61F 2310/00796* (2013.01)

(58) Field of Classification Search
CPC ..... A61F 2/06; A61F 2/07; A61F 2002/0077; A61F 2/28; A61F 2/30
USPC ........ 623/1.15, 1.16, 1.41–1.46, 11.11, 16.11
See application file for complete search history.

(56) References Cited

U.S. PATENT DOCUMENTS

2008/0206297 A1   8/2008   Roeder et al.

FOREIGN PATENT DOCUMENTS

| EP | 0681845 A2 | 11/1995 |
|----|------------|---------|
| EP | 1958595 A1 | 8/2008 |
| GB | 2045082 A | 10/1980 |

(Continued)

OTHER PUBLICATIONS

"International Application Serial No. PCT/US2011/060379, International Search Report mailed Mar. 20, 2012", 6 pgs.

(Continued)

*Primary Examiner* — Jason-Dennis Stewart
(74) *Attorney, Agent, or Firm* — Schwegman Lundberg & Woessner, P.A.

(57) ABSTRACT

The present disclosure relates to orthopedic implants including a porous, non-metallic, bone interface or outer bone contacting surface adapted for promoting bone ingrowth into the pores of such surface. The present disclosure also relates to orthopedic implants having a porous, non-metallic and/or polymeric bone interface or outer bone contacting surface wherein the implant has a stiffness that approaches or substantially matches the stiffness of the surrounding bone and thereby reduces the effects of stress shielding. The present disclosure also relates to methods of making such implants.

20 Claims, 6 Drawing Sheets

(56) References Cited

FOREIGN PATENT DOCUMENTS

| | | |
|---|---|---|
| WO | WO-0213730 A2 | 2/2002 |
| WO | WO-0217820 A1 | 3/2002 |
| WO | WO-2012065068 A1 | 5/2012 |

OTHER PUBLICATIONS

"International Application Serial No. PCT/US2011/060379, Invitation to Pay Additional Fees mailed Feb. 2, 2012", 6 pgs.

"International Application Serial No. PCT/US2011/060379, Written Opinion mailed Mar. 20, 2012", 8 pgs.

ORTHOPEDIC IMPLANT WITH POROUS POLYMER BONE CONTACTING SURFACE

CROSS REFERENCE TO RELATED APPLICATION(S)

This application is a U.S. National Stage Filing under 35 U.S.C. §371 of International Patent Application Serial No. PCT/US2011/060379, filed on Nov. 11, 2011, published on May 18, 2012 as WO 2012/065068 A1, which claims the benefit of priority under 35 U.S.C. §119(e) of U.S. Provisional Application Ser. No. 61,412,510, filed Nov. 11, 2010, the benefit of priority of each of which is claimed hereby and each of which is hereby incorporated by reference in its entirety.

FIELD OF THE DISCLOSURE

The present disclosure generally relates to orthopedic implants having a porous bone interface or outer bone contacting surface. More particularly, the present disclosure relates to orthopedic implants including a porous, non-metallic, bone interface or outer bone contacting surface adapted for promoting bone ingrowth into the pores of such surface. Even more particularly, the present disclosure relates to orthopedic implants having a porous, polymeric outer bone contacting surface that is adapted for promoting bone ingrowth. The present disclosure also relates to orthopedic implants having a porous, non-metallic and/or polymeric bone interface or outer bone contacting surface wherein the implant has a stiffness that approaches or substantially matches the stiffness of the surrounding bone and thereby reduces the effects of stress shielding. The present disclosure also relates to methods of making such implants.

BACKGROUND

Orthopedic (bone) implants are commonly used to replace some or all of a patient's joint, such as a hip, knee, shoulder or elbow, where deterioration of or damage to the joint due to aging, illness, injury or trauma is present. These implants are designed to accommodate the normal movements and stresses associated with such joints and to provide increased mobility and relief from pain. Orthopedic implants are most typically constructed of metal, polymeric material or some combination thereof.

Proper fixation of the implant within the bone is an extremely important aspect of joint replacement inasmuch as long-term implant success is dependent, in large part, on the implant remaining relatively stationary within the implantation site. Proper and reliable fixation of the implant allows bone tissue to grow into and around the implant to establish long-term fixation of the implant within the bone.

Typically, initial stabilization of the implant is achieved by applying bone cement (e.g., polymethylmethacrylate (PMMA)) during surgery. Bone cement acts as filler between the bone and the implant. However, long term stabilization of the implant is often achieved and dependent on osseointegration (i.e., bone tissue ingrowth into the implant) of the implant with the surrounding bone of the patient. Accordingly, orthopedic implants are commonly provided with an outer bone contacting surface adapted for allowing bone ingrowth. For example, implants may be provided with a porous bone contacting surface which would allow bone tissue ingrowth over time. This porous bone contacting surface may be provided during manufacture of the implant or incorporated into the implant in a post-molding treatment.

As noted above, while proper fixation of the orthopedic implant is an important aspect of the joint replacement surgery, post-surgical considerations also play a role in achieving successful longer term joint replacement. Natural bone requires that it be cyclically stressed to survive and remain strong as bone that is not subjected to normal stresses and loads will lose bone density and weaken. Some orthopedic implants that include a metal component may result in an implant which has an elastic modulus that is much greater than that of cortical bone. Therefore, the implant is much stiffer than the bone in which it is to be implanted. A large difference in the elastic modulus of the implant on the one hand and the bone on the other may cause the implant (rather than the bone) to support and absorb most of the loads imparted on a joint, leaving the bone virtually unloaded or unstressed. This phenomenon, which is commonly referred to as stress shielding, can result in the formation of debris around the implantation site, bone loss and/or bone resorption.

Accordingly, orthopedic implants with metal have been developed that reduce or otherwise limit the effects of stress shielding. One example of such an implant is the EPOCH® hip prosthesis available from Zimmer, Inc., of Warsaw, Ind. The EPOCH® hip stem has a porous surface that allows for fixation of the implant in the femur through natural bone tissue ingrowth. In addition, the EPOCH® hip stem is made of materials that closely match the stiffness of bone. The EPOCH® device includes a metal core made of a cobalt-chromium-molybdenum alloy, a middle portion made of a high strength thermoplastic material and an outer surface layer made of a titanium fiber metal mesh. The fiber metal mesh provides a porous bone contacting surface that allows for bone growth into the implant while the overall construction of the hip stem provides a stiffness comparable to the stiffness of a normal femur, thereby reducing the potential for stress shielding.

Metallic porous bone contacting surfaces may also include pads or beads embedded in the body of the implant. Examples of implants that include such porous, metallic surface layers, including fiber metal mesh of the type described above, are disclosed in U.S. Pat. Nos. 5,219,363, 5,236,457, 5,443,512 and 6,740,186 all of which are herein incorporated by reference in their entireties.

While systems such as the EPOCH® hip stem have proven to be commercially successful and have effectively addressed bone fixation and stress shielding, use of non-metallic materials in the bone contacting surfaces of orthopedic implants has also been considered. Thermoplastics, thermoplastic composites, ceramics and other non-metallic materials may be suited to match the stiffness of bone and thereby limit the effects of stress shielding. These materials may also be provided with a porous structure to allow for bone ingrowth and aid in implant fixation. In addition, some of these materials are often advantageously shaped by economical molding processes such as injection molding or compression molding. Examples of such implants and methods are described below.

SUMMARY

In one aspect, the present disclosure is directed to an orthopedic device for implantation into bone tissue. The device includes a bone fixation member having an outer polymeric body surrounding at least a portion of a core. The outer polymeric body includes an inner portion and an outer portion. The outer portion defines a, porous bone contacting surface adapted for tissue ingrowth. The outer portion has a greater porosity than the inner portion.

In another aspect, the present disclosure relates to a method of making an implantable orthopedic device. The method includes the steps of introducing a first polymer into a mold to provide a polymeric body having at least an inner portion and an outer portion. The outer portion includes a bone contacting surface. The method further includes forming pores in the bone contacting surface.

Disclosed herein are orthopedic devices, more specifically implants, with a bone fixation member having bone interfaces or outer bone contacting surfaces that are porous and allow for bone tissue ingrowth from the adjacent natural bone. Preferably, the bone interface or outer bone contacting surface (i.e., surface that faces and is adjacent to natural bone of the subject) of such implants is at least substantially free of metal and/or metal components. More preferably, the outer bone contacting surfaces are entirely free of metal i.e., non-metallic. In one embodiment, the implant includes an outer, non-metallic or substantially metal-free bone contacting surface made of a biocompatible material that is adapted for pore formation. The material may be such that pores are introduced during formation (such as during molding) of the bone contacting surface or, alternatively, the bone contacting surface may be formed and subsequently treated to introduce pores into at least a portion of the surface.

The biocompatible, non-metallic or substantially metal-free material of the bone contacting surface may be or include, for example, a thermoplastic or other type of polymer. Where the bone contacting surface is a polymer, suitable polymers include certain organic polymer thermoplastics such as, but not limited to, polyaryletherketones ("PAEK"), and more particularly, polyetheretherketone ("PEEK"), and polyetherketoneketone ("PEKK"). Other suitable materials include self-reinforced polyphenylene ("SRP") as well as other polymeric materials that may or may not be injection moldable including, but not limited to ultra-high molecular weight polyethylene polymer material ("UHMWPE").

Orthopedic implants of the type described herein may have pores distributed across substantially the entire implant, but more preferably across at least selected regions of the outer bone contacting surface. The pores may be substantially uniformly distributed or may be unevenly and/or selectively distributed. For example, as described below, the outer bone contacting surface of the implant may have a greater porosity than the interior portion(s) of the implant. Stated differently, the inner portion of the implant may be non-porous or substantially non-porous (e.g., not allow bone ingrowth). Also, the porosity may vary between different portions of the implant. In addition, certain or selected portions of the outer bone contacting surface may have a greater concentration of pores or porosity than other portions. For example, those selected portions of the outer bone contacting surface that will be adjacent to or in close proximity to the natural bone tissue of the patient may include a greater density or distribution of pores to allow for greater bone ingrowth.

Orthopedic implants of the present invention preferably include a polymeric body that defines a bone contacting surface. The implant may further include a core that is at least partially surrounded by or otherwise substantially encased within polymeric body. The polymeric body includes an inner portion and outer portion. The outer portion defines the bone contacting surface. The inner portion is preferably made substantially of a biocompatible polymer that is suitable for use with and can bond or otherwise attach directly or indirectly to the core. Similarly, the polymer selected is compatible with and will bond to the polymer(s) of the outer portion. Preferably, the biocompatible polymer is one that is moldable by injection molding, insert molding, over molding, two shot molding, sandwich molding, co-injection molding or any other suitable molding techniques.

Orthopedic implants in accordance with the present invention may be constructed of a combination of materials, depending on their use as implants. For example, the implant may include a core preferably made of a biocompatible metal of the type often employed for implants such as titanium, titanium alloy, cobalt-chromium, cobalt chromium molybdenum, tantalum and a polymeric body. As described above, the polymeric body may itself be made of one or more different polymer materials. Thus, the entire polymeric body may be made of a single polymer wherein the polymeric body has different or varying degrees of porosity throughout. Alternatively, the inner portion may be made of a first polymeric material and the outer portion may be made of a second polymeric material that is either different from the first material or has a different porosity. More specifically, the first polymeric material of the inner portion is substantially non-porous/solid or less porous than the outer portion while the outer portion may be made of a different polymeric material which includes a bone contacting surface that is porous and/or adapted for pore formation. Alternatively, the orthopedic implant may not include a core, but may simply be made of at least two different polymers or the same polymer having different or varying degrees of porosity, with a porous outer portion having a bone contacting surface and the less porous or non-porous polymer defining the inner portion of the implant.

Alternatively, the implant may include a core and polymeric body having multiple and/or alternating/regions of porous and non-porous/solid or less porous polymer. The polymeric body may include an inner portion, an outer portion and an intermediate portion where the intermediate portion includes at least one region or layer that is substantially porous and at least one region or layer that is substantially non-porous/solid or less porous. While interior layers or regions of porous polymer that are surrounded by solid layers or regions may not necessarily allow for bone growth, they do provide other advantages. For example, implants having a distribution of regions/layers with varying degrees of porosity may provide for a lighter-weight implant or an implant with a desired modulus of elasticity that may reduce or lessen the effects of stress-shielding on the user.

The inner portion is preferably non-porous/solid and is made of at least one biocompatible polymer, or a blend of polymers. Preferably, the polymers selected are thermoplastic polymers that are suitable for use in injection molding. Examples of such polymers include, but are not limited to a PAEK, such as PEEK, PEKK, or SRP. The inner portion may be made from polymeric materials which are not typically injection molded including, but not limited to UHMWPE. The biocompatible polymer of the inner portion may be another polyolefin, or a polyester, polyimide, polyamide, polyacrylate, and/or other suitable polymers.

The porous bone contacting or fixation surface of the polymeric outer portion may be formed during processing (e.g., molding) by combining the polymer with a blowing, foaming or expanding agent, known as a pore former. The pore former helps the formation of pores in a polymer through the release of a gas during processing. Depending on the size and nature of the implant, the outer portion is preferably about 1-5 mm thick and more preferably, about 1-3 mm in order to allow maximum bone ingrowth. Preferably, the outer portion may have a porosity as low as about 55, 65, or 75 percent by volume or as high as about 80, 85, or 90 percent by volume. The porosity percentage may be calculated by dividing the measured volume of pores within a certain volume by the total volume. It may be preferred that the pores have a size of at least about 300 µm in order to enhance bone ingrowth or ongrowth; however, it will be appreciated that other pore sizes may be used and not depart from the spirit and scope of the present disclosure.

For some applications, only selected regions of outer portion need be porous and provide the bone contacting surface. For example, the bone contacting surface may be located in those portions of the implant where bone ingrowth is desired and/or is most likely to occur.

Turning now to the method of making implants in accordance with the present invention, the polymeric bone contacting surface of the implant may be formed through the use of foaming agents or blowing agents, i.e., pore formers. A foaming agent or blowing agent is an agent that leads to the formation of pores in the polymer through the release of a gas during processing. Other methods of introducing pores into a polymer are known and will be appreciated by those skilled in the art.

The injection molding process useful in making implants in accordance with the present disclosure may utilize the fountain flow effect to provide implants having both solid/non-porous and porous portions. Briefly, in the fountain flow effect, as a mold or die "D" is filled with a first polymer melt, the melt moves from the stream's center line toward the die wall or other solid surfaces (e.g., metal core of the implant) within the die wherein it cools rapidly and freezes to form an outer coating or skin. The skin is formed because the walls or surfaces of the die or core are below the transition temperature of the melt and the portion of the melt that interacts with the wall cools rapidly and freezes to create the skin. The process may also include injecting a second shot of polymer melt into the die which further displaces or otherwise moves the first polymer melt towards the inner surfaces defining the mold cavity of the die. These processes typically result in an end product that has a sandwich-like structure with the first polymer melt surrounding the second polymer melt.

In order to expose the pores which further promote bone ingrowth, at least a portion of the polymeric body 24, i.e., the skin, is preferably removed to expose the pores and provide the porous bone contacting surface. The removal process may be performed by machining, grinding, sanding or any other method as will be appreciated by those of skill in the art to expose the pores of the polymeric bone contacting surface.

Preferably in the "two-shot" process, the first melt is a non-porous polymer and the second polymer melt is a pore forming melt. The pore forming melt is a combination of a pore forming agent such as a blowing or expanding agent and a polymer. The pore forming agent may be a supercritical fluid ("SCF") derived from an atmospheric gas such as carbon dioxide or nitrogen. The pore forming agent is injected directly into the polymer in order to form a single phase pore forming melt which can be then injected into the die.

BRIEF DESCRIPTION OF THE FIGURES

In the course of this description, reference will be made to the accompanying drawing(s), wherein.

DETAILED DESCRIPTION

As required, detailed embodiments of the present disclosure are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in any appropriate manner.

Figure 1:
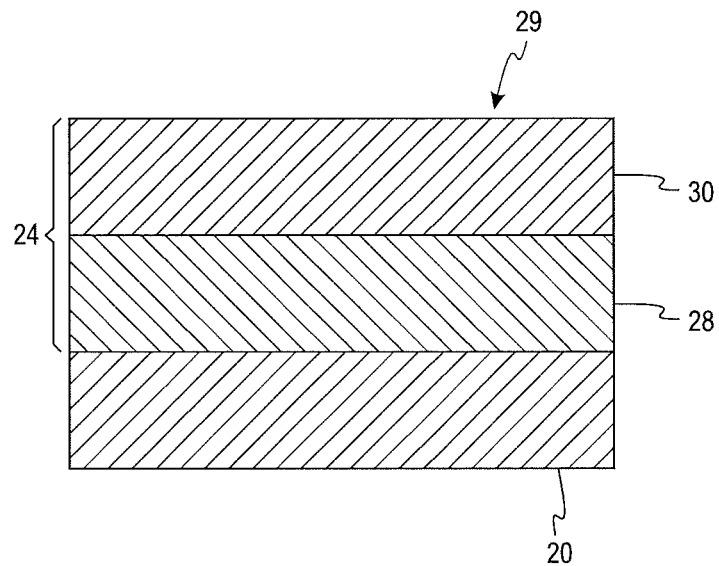
FIG. 1 is a schematic, cross-sectional view of a section of one side of one embodiment of an implant made in accordance with the present disclosure.
Figure 2:
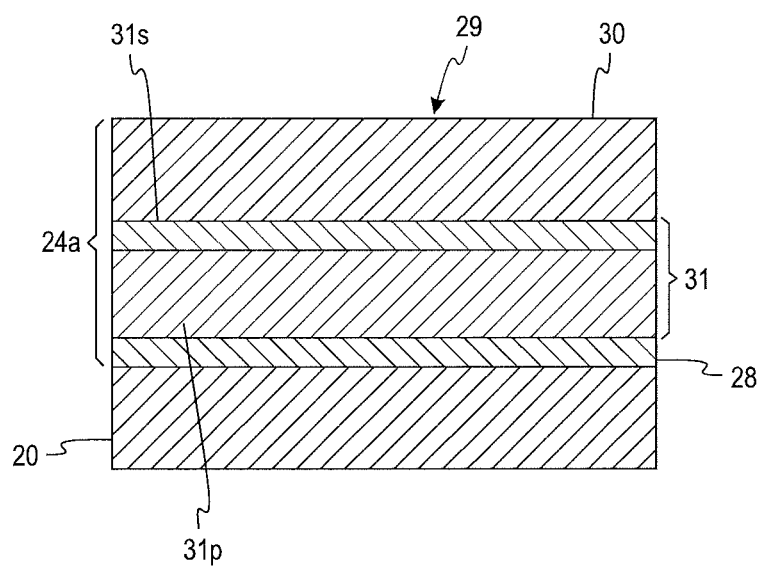
FIG. 2 is a schematic, cross-sectional view of a section of one side of another embodiment of an implant made in accordance with the present disclosure.

With reference to the embodiment of FIG. 1, orthopedic implants 10 of the present disclosure includes a polymeric body 24 that defines a bone contacting surface 29. The implant may further include a core 20 that is at least partially surrounded by or otherwise substantially encased within polymeric body 24. It will be appreciated that FIGS. 1 and 2 depict, in cross section, one side of the implant or a complete implant having only one bone-contacting surface in cross section. Thus, in the case where the implant includes a central core (as in the hip stem implants described in the embodiments below), a full cross-sectional view of the implant would likewise show the polymeric body 24 on the other side of (i.e., below) core 20.

With further reference to FIG. 1, polymeric body 24 includes an inner portion 28 and outer portion 30. The outer portion 30 defines the bone contacting surface 29. Inner portion 28 is made substantially of a biocompatible polymer that is suitable for use with and can bond or otherwise attach directly or indirectly to core 20, if any. Similarly, the polymer selected is compatible with and will bond to the polymer(s) of outer portion 30, discussed below. Preferably, the biocompatible polymer is one that is moldable by injection molding, insert molding, over molding, two shot molding, sandwich molding, co-injection molding or any other suitable molding techniques.

Orthopedic implants in accordance with the present disclosure may be constructed of a combination of materials, depending on their use as implants. For example, as illustrated schematically in FIG. 1, the implant may include a core 20 preferably made of a biocompatible metal of the type often employed for implants such as titanium, titanium alloy, cobalt-chromium, cobalt chromium molybdenum, tantalum and a polymeric body 24. As described above, polymeric body 24 may itself be made of one or more different polymer materials. Thus, the entire polymeric body 24 may be made of a single polymer wherein polymeric body 24 has different or varying degrees of porosity throughout. Alternatively, inner portion 28 may be made of a first polymeric material and outer portion 30 may be made of a second polymeric material that is either different from the first material or has a different porosity. More specifically, the first polymeric material of inner portion 28 is substantially non-porous/solid or less porous than the outer portion 30 while the outer portion 30 may be made of a different polymeric material which includes bone contacting surface 29 that is porous and/or adapted for pore formation. In other embodiments, the orthopedic implant may not include a core, but may simply be made of at least two different polymers or the same polymer having different or varying degrees of porosity, with a porous outer portion 30 having a bone contacting surface 29 and the less porous or non-porous polymer defining the inner portion 28 of the implant.

In an alternative embodiment, as illustrated schematically in FIG. 2, the implant may include a core 20 and polymeric body 24a having multiple and/or alternating/regions of porous and non-porous/solid or less porous polymer. Polymeric body 24a may include an inner portion 28, an outer portion 30 and an intermediate portion 31. The porous outer portion 30 includes bone contacting surface 29. The intermediate portion 31 includes at least one region or layer 31p that is substantially porous and at least one region or layer 31s that is substantially non-porous/solid or less porous than region 31p. While the illustrated intermediate portion includes two regions or layers, it will be appreciated that it may have any number of regions or layers with varying degrees of porosity. The inner portion 28 and solid layer 31s may be substantially non-porous/solid, while the outer portion 30 and the porous polymeric layer 31p may be substantially porous. As with the example of FIG. 1, an implant such as this may or may not have an inner core 20. While interior layers or regions of porous polymer, such as region/layer 31p, that are surrounded by solid layers or regions may not necessarily allow for bone growth, they do provide other advantages. For example, implants having a distribution of regions/layers with varying degrees of porosity, as shown in FIG. 2, may provide for a lighter-weight implant or an implant with a desired modulus of elasticity that may reduce or lessen the effects of stress-shielding on the user.

In one exemplary embodiment, the inner portion 28 (FIGS. 1 and 2) is formed of a material that provides strength to the implant without increasing and, more preferably, reducing the effect of stress shielding. As noted above, the inner portion is preferably non-porous/solid and is made of at least one biocompatible polymer, or a blend of polymers. Preferably, the polymers selected are thermoplastic polymers (previously identified) that are suitable for use in injection molding. Examples of such polymers include, but are not limited to a PAEK, such as PEEK, PEKK, or SRP. In another exemplary embodiment, inner portion 28 may be made from polymeric materials which are not typically injection molded including, but not limited to UHMWPE. In other exemplary embodiments, the biocompatible polymer of the inner portion 28 may be another polyolefin, or a polyester, polyimide, polyamide, polyacrylate, and/or other suitable polymers.

The outer portion 30 (FIGS. 1 and 2) is also made of a biocompatible polymer that is compatible with the material selected for the inner portion 28 and intermediate portion 31, if any, such that the two materials form an integral polymeric body 24. Alternatively, the polymer is selected to be used with and possibly attached directly or indirectly to a core, if any. In one example, outer portion 30 may be made from PMMA. Other polymers suitable for use as an outer portion include, but are not limited to, PAEK, such as PEEK or PEKK and other polymeric materials that may or may not be injection moldable including, but not limited to UHMWPE. The intermediate portion 31 may be made from any of the materials or combination of materials used for the inner and outer portions.

As discussed in further detail below, the porous bone contacting or fixation surface 29 of the polymeric outer portion 30 may be formed during processing (e.g., molding) by combining the polymer with a blowing, foaming or expanding agent, known as a pore former. The pore former helps the formation of pores 32 (See FIGS. 3-5) in a polymer through the release of a gas during processing. In one embodiment and depending on the size and nature of the implant, the outer portion 30 is about 1-5 mm thick and more preferably, about 1-3 mm in order to allow maximum bone ingrowth. Preferably, the outer portion 30 may have a porosity as low as about 55, 65, or 75 percent by volume or as high as about 80, 85, or 90 percent by volume. The porosity percentage may be calculated by dividing the measured volume of pores within a certain volume by the total volume. It may be preferred that the pores have a size of at least about 300 μm in order to enhance bone ingrowth or ongrowth; however, it will be appreciated that other pore sizes may be used and not depart from the spirit and scope of the present disclosure.

Figure 3:
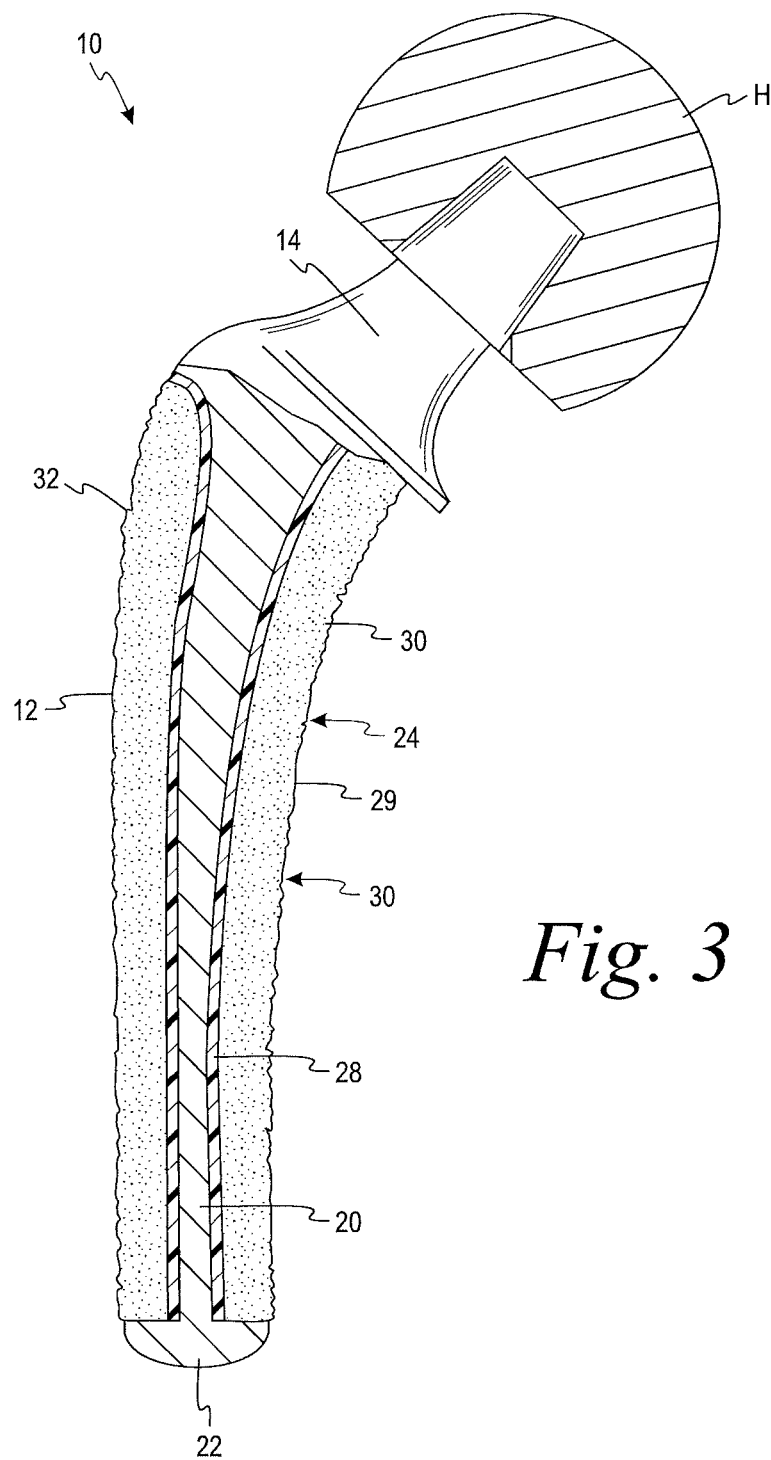
FIG. 3 is a cross sectional view of one embodiment of an orthopedic implant in the form of a hip stem made in accordance with the present disclosure.

FIG. 3 illustrates an exemplary implantable orthopedic implant 10a in the form of a femoral hip stem provided in accordance with the present disclosure. However, those skilled in the art will appreciate that the present disclosure may be applied to other orthopedic devices for which it is desirable to have a porous outer bone contacting or fixation surface to allow for bone ingrowth, for example, a femoral condylar knee implant.

As shown in FIG. 3, the hip stem 10a generally includes an elongated body 12 and a neck 14. Neck 14 is positioned at a proximal end of the body 12 and is adapted to fixedly receive a modular head ("H") of a hip prosthetic. It will be appreciated that the hip stem and body may be provided as a unitary structure. Body 12 includes inner core 20 which extends distally from the neck 14 to integral end cap 22. Inner core 20 may be substantially encased (i.e., except for end cap 22 and neck 14, which may remain exposed) or may otherwise be covered with a suitable biocompatible material, preferably made of one or more polymers described above, to define polymeric body 24. In the embodiment illustrated in FIG. 3, polymeric body 24 includes an inner portion 28 and an outer portion 30. The outer portion 30 includes a bone contacting or fixation surface 29 with pores 32 that allow for bone tissue ingrowth or cement infiltration once the orthopedic implant has been implanted into a subject. Inner and outer portions 28 and 30 may be made of the same or different polymers as shown and previously described in connection with FIG. 1.

Figure 4:
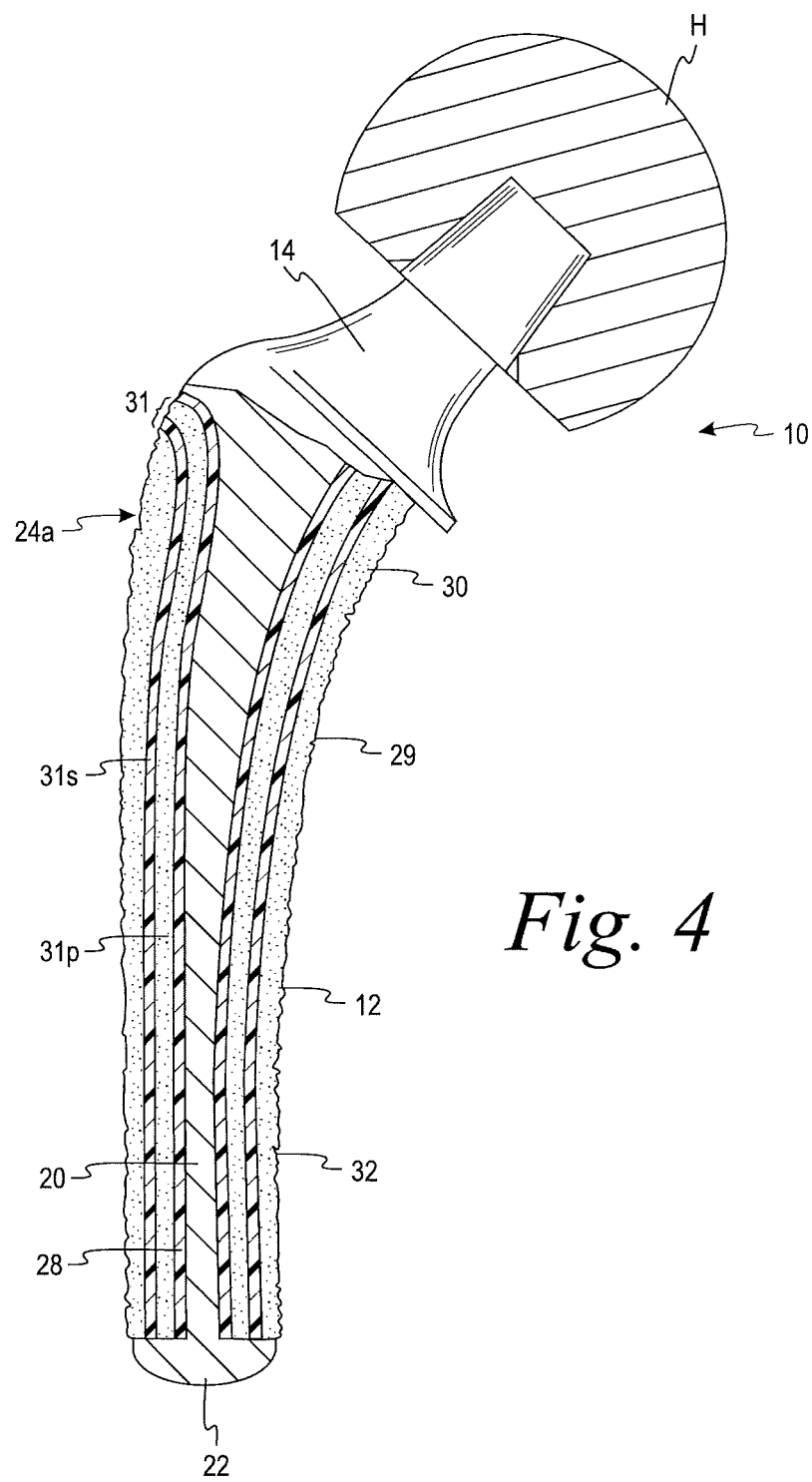
FIG. 4 is a cross sectional view of another embodiment of an orthopedic implant in the form of a hip stem made in accordance with the present disclosure.

FIG. 4 shows an implantable orthopedic implant, also in the form of a femoral hip stem, where the implant 10b has multiple and/or alternating regions, portions or layers of porous and substantially non-porous polymer as shown in and described in connection with the schematic of FIG. 2 The polymeric body 24 includes a solid/non-porous inner portion 28, an intermediate portion 31 and a porous outer portion 30 providing a porous bone contacting or fixation surface 29. The intermediate portion 31 includes at least one porous region or layer 31p and at least one substantially solid/non-porous or less porous region or layer 31s.

Figure 5:
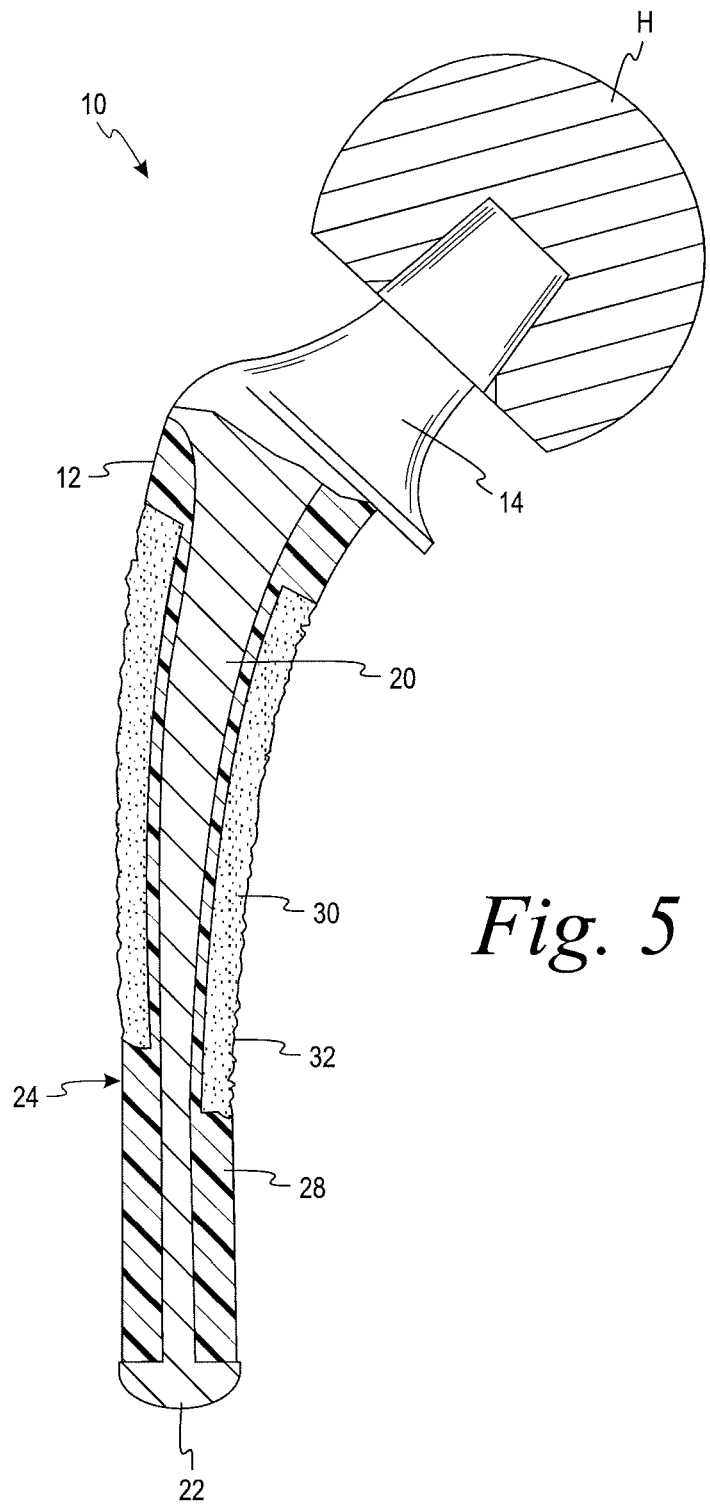
FIG. 5 is a cross sectional view of yet another embodiment of an orthopedic implant in the form of a hip stem made in accordance with the present disclosure.

In yet another embodiment, shown in FIG. 5, only selected regions of outer portion 30 may be porous and provide the bone contacting surface 32. In the embodiment of FIG. 5, bone contacting surface 32 may be located in those portions of the implant and more specifically body 12 where bone ingrowth is desired and/or is most likely to occur.

Regarding all of the embodiments, core 20 and neck 14 are preferably constructed of any of the common biocompatible materials generally employed for implants including but not limited to titanium, titanium alloy, cobalt-chromium alloy, and composite materials.

As mentioned above, when the implant includes pores on its outer bone-contacting surface, bone-bonding is achieved by the growth of natural bone tissue into the pores to provide a mechanical interlock. Therefore, in accordance with the present disclosure, it is preferable to provide a polymeric bone contacting surface with pores sufficiently sized to allow for bone ingrowth.

Figure 6:
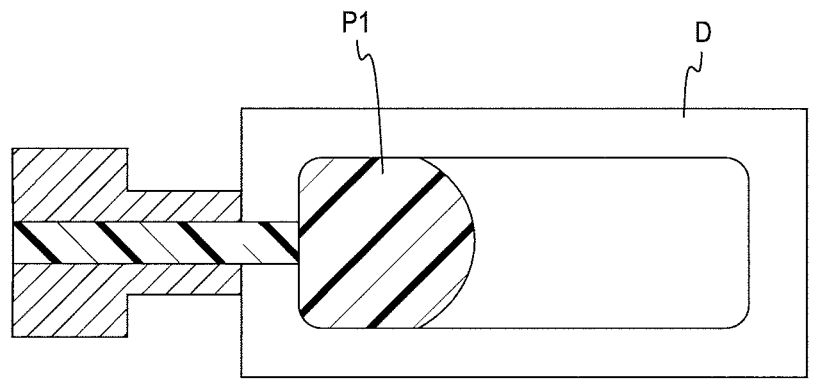
FIG. 6 is a representation of one step of the injection molding process in accordance with the one embodiment of the present disclosure.
Figure 7:
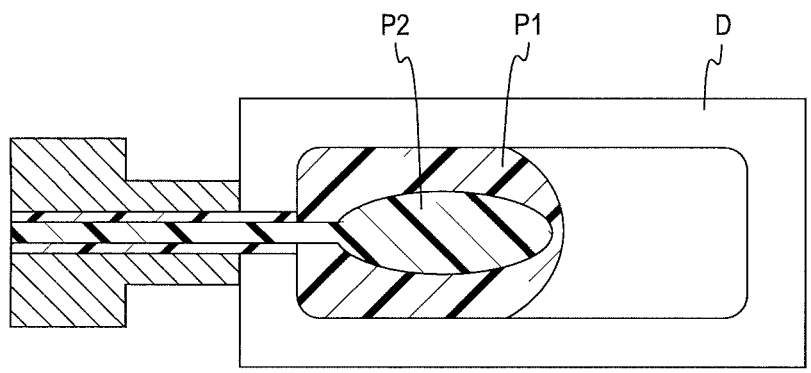
FIG. 7 is a representation of another step of the injection molding process in accordance with the one embodiment of the present disclosure.
Figure 8:
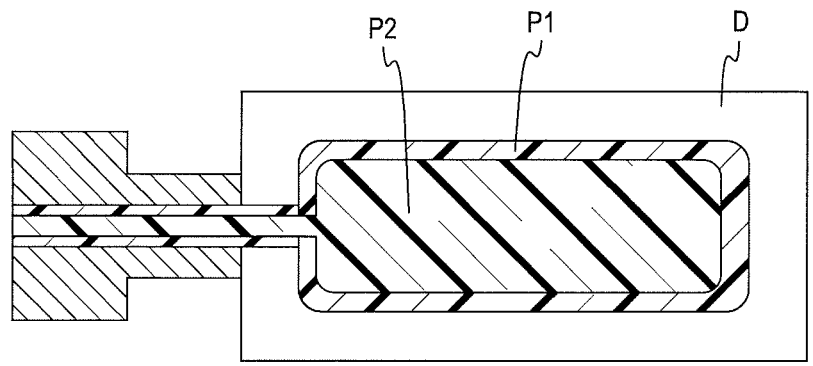
FIG. 8 is a representation of yet another step of the injection molding process in accordance with the one embodiment of the present disclosure.

The injection molding process useful in making implants in accordance with the present disclosure may utilize the fountain flow effect to provide implants having both solid/non-porous and porous portions. FIGS. 6-8 generally illustrate the fountain flow effect. Briefly, in accordance with the fountain flow effect, as a mold or die "D" is filled with a first polymer melt P1, the melt moves from the stream's center line toward the die wall or other solid surfaces (e.g., metal core 20 of the implant) within the die wherein it cools rapidly and freezes to form an outer coating or skin. See FIG. 6. The skin is formed because the walls or surfaces of the die or core are below the transition temperature of the melt and the portion of the melt that interacts with the wall cools rapidly and freezes to create the skin. The process may also include injecting a second shot of polymer melt P2 into the die which further displaces or otherwise moves the first polymer melt P1 towards the inner surfaces defining the mold cavity of the die. See FIG. 7. These processes typically result in an end product that has a sandwich-like structure with the first polymer melt P1 surrounding the second polymer melt P2. See FIG. 8.

Figure 9:
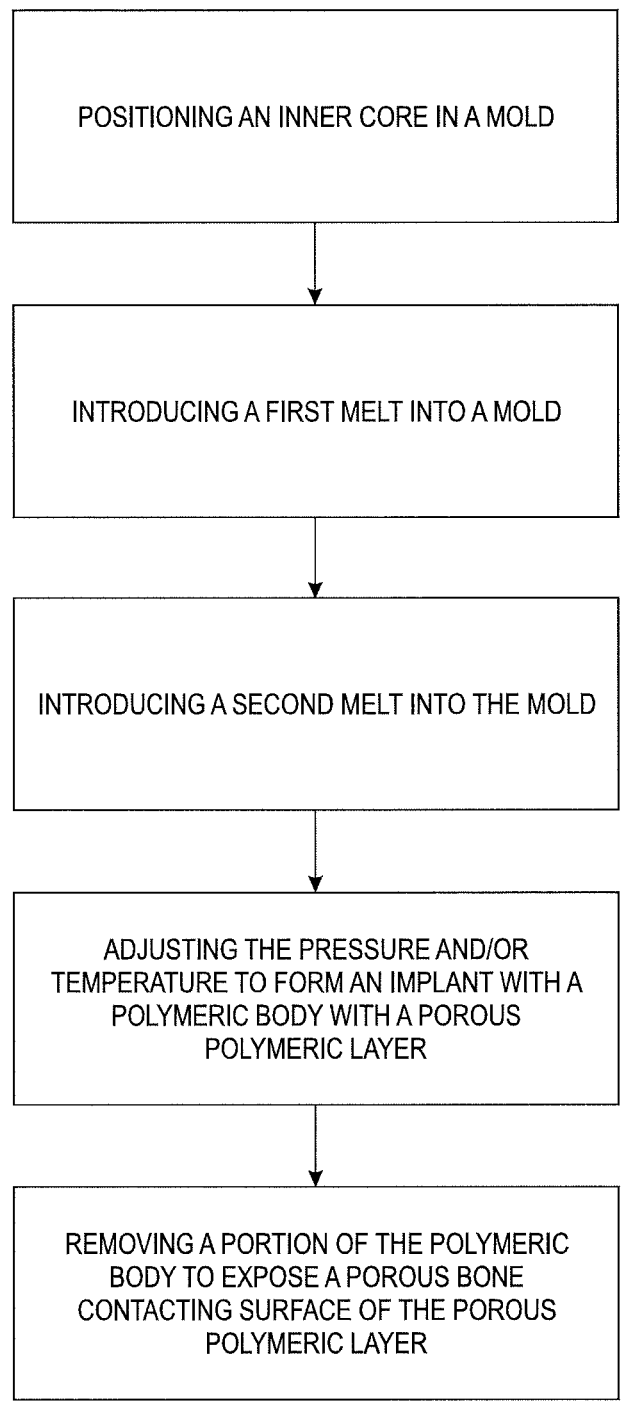
FIG. 9 is a diagrammatic view of a method for making an implantable orthopedic device.

According to one embodiment, diagrammatically depicted in FIG. 9, a "two shot" injection molding method is used to manufacture an orthopedic implant such as the hip stem of the present disclosure. The method incorporates the MUCELL™ process available from Trexel of Woburn, Mass. In accordance with the method, the internal core 20 of the implant is situated or placed within a die of a molding device, preferably an injection molding device. A shot of a first polymer melt is injected into the die and is followed by a shot of a second polymer melt. Due to the fountain flow effect, at least a portion of the first polymer melt is frozen against the walls of the die and against the outer surface of the internal core, thus forming a non-porous skin. The second polymer melt is back-filled into the mold and continues to push the first polymer melt outwardly within the die. Injecting these melts in the manner described above, results in a polymeric body 24 which overlays the core 20. The core 20 and polymeric body 24 are then removed from the die and cooled to room temperature.

In order to expose the pores which further promote bone ingrowth, at least a portion of the polymeric body 24, i.e., the skin, is preferably removed to expose the pores and provide the porous bone contacting surface shown in FIGS. 3-5 and schematically depicted in FIGS. 1 and 2. The removal process may be performed by machining, grinding, sanding or any other method as will be appreciated by those of skill in the art to expose the pores of the polymeric bone contacting surface.

In one embodiment of a "two-shot" process, the first melt is a non-porous polymer and the second polymer melt is a pore forming melt. The pore forming melt is a combination of a pore forming agent such as a blowing or expanding agent and a polymer. The pore forming agent may be a supercritical fluid ("SCF") derived from an atmospheric gas such as carbon dioxide or nitrogen. The pore forming agent is injected directly into the polymer in order to form a single phase pore forming melt which can be then injected into the die.

As described above, the first shot of non-porous polymer is introduced into the mold and freezes against the inner surface of the mold and the outer surface of core 20, thereby forming a skin. The pore forming melt is injected immediately behind the first shot of polymer. The interim implant thus includes the frozen and thus solid skin layer of the pore forming melt, overlying the non-frozen and porous portion 30, which in turn overlies the frozen (solid) region 28 that is bonded to core 20. Once the outer frozen (solid) skin layer (not shown) is removed (e.g., by grinding, machining, etc.), the polymeric body includes an outer porous portion 30 with a porous bone contacting surface 29 over a solid inner portion 28, as shown schematically in FIG. 1 and more particularly in FIG. 3.

In another embodiment of the "two shot" process, the first melt is a pore forming melt and the second melt is a non-porous polymer. Although the first shot of the pore forming melt is "porous," contact with the metal surface of the mold and core 20 causes the melt to freeze and solidify. Thus, the regions of the pore forming melt adjacent the inner wall of the mold and the outer surface of core 20 are non-porous or solid, while regions spaced away from the metal surfaces retain their porosity. The second shot of substantially non-porous or solid polymer follows the first shot and forms a region of solid polymer, such as layer 31s shown in FIG. 4. Once the outer frozen skin layer (not shown) is removed, the polymeric body includes an outer porous portion 30b with a porous bone contacting surface 29, a solid inner portion 28a, solid outer portion 28b, and an inner porous portion 30.

Alternatively, a "one shot" injection molding process can be used. Again, in one embodiment the process may use the MUCELL™ molding process available from Trexel of Woburn, Mass. However, only a pore forming melt is introduced into the mold as a single injection. The SCF converts to gas and create pores within the polymer of the pore forming melt. Injecting this melt results in a polymeric body 24 which overlays the core 20. The core 20 and polymeric body 24 are then removed from the mold and cooled to room temperature. At least a portion of the outer (frozen) polymeric body 24, i.e., skin, is removed to expose pores at the bone contacting region 30. FIG. 3 is also illustrative of an implant made according to the above "one shot" method. With the outer frozen layer removed, the polymeric body 24 includes a solid polymeric inner portion 28 and an outer polymeric porous portion 30 providing a polymeric porous bone contacting surface 29.

It is noted that the pore forming solution (including the SCF) of the present disclosure may be more viscous than standard polymers used for orthopedic implants which allows lower pressures to be used during the injection molding process. This allows smaller injection molding machines to be used which reduces manufacturing costs. In addition, the porosity of the outer portion reduces the amount of polymer material required for the orthopedic device. Therefore, manufacturing costs are reduced using the methods disclosed herein. Less material and a lighter and less dense implant also assist in allowing more of the stresses to be transmitted to the natural bone, thereby reducing the effects of stress shielding.

It will be appreciated that with the methods disclosed herein, the materials and configurations can be manipulated in order to control the pore size of the porous outer portion of the orthopedic device. For example, the amounts of the polymer and SCF and the temperature and pressure during the molding process can be adjusted in order to obtain the desired porosity. In addition, the material and thickness of the inner core can also be adjusted in order to obtain the desired strength for a certain orthopedic device.

To further promote bone ingrowth into the orthopedic device, the outer portion and, more specifically, the porous polymeric bone contacting surface may be treated with calcium phosphate ceramics, for example hydroxyapatite. Such a treatment may be performed using any standard application process.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description, and it is understood that any claims may be directed to the features hereof, including as combinations of features that are individually disclosed or claimed herein.

What is claimed is:

1. An orthopedic device for implantation into bone tissue comprising:
    a bone fixation member having a core; and
    an outer polymeric body surrounding at least a portion of the core;
    the outer polymeric body including:
        an inner portion;
        an outer portion further defining a porous bone contacting surface adapted for bone tissue ingrowth, wherein the outer portion has a greater porosity than the inner portion; and
        an intermediate portion positioned between the inner portion and the outer portion, wherein the intermediate portion includes a first region and a second region, and wherein the first region is positioned between the inner portion and the second region and has a greater porosity than the inner portion and the second region.

2. The orthopedic device of claim 1, wherein the inner portion, the intermediate portion, and the outer portion of the polymeric body comprise a unitary structure.

3. The orthopedic device of claim 1, wherein the inner portion and the second region are solid polymers.

4. The orthopedic device of claim 1, wherein the second region is a solid polymer region and the first region is a porous polymer region.

5. The orthopedic device of claim 1, wherein the inner portion and the second region are substantially non-porous and the outer portion and the first region are substantially porous.

6. The orthopedic device of claim 1, wherein the polymeric body is formed of at least one of polymethacrylate, polyaryletherketone, polyetheretherketone, polyetherketoneketone, self reinforced polyphenylene, and ultra-high molecular weight polyethylene.

7. The orthopedic device of claim 1, wherein the core is formed of at least one of titanium, titanium alloy, and cobalt-chromium alloy.

8. The orthopedic device of claim 1, wherein at least a portion of the porous bone contacting surface includes a surface treatment selected to enhance bone tissue ingrowth.

9. The orthopedic device of claim 8, wherein the surface treatment is hydroxyapatite.

10. A method for making an implantable orthopedic device, comprising:
    introducing a first polymer into a mold;
    introducing a second polymer into the mold to force the first polymer to an interior surface of the mold to provide a polymeric body having an inner portion and outer portion, the outer portion comprising a polymeric bone contacting surface;
    forming pores in at least the bone contacting surface; and
    exposing the pores of the polymeric bone contacting surface.

11. The method of claim 10, wherein the first polymer is selected from the group consisting of polymethacrylate, polyaryletherketone, polyetheretherketone, polyetherketonekeytone, and self reinforced polyphenylene.

12. The method of claim 10, wherein the second polymer is selected from the group consisting of polymethacrylate, polyaryletherketone, polyetheretherketone, polyetherketoneketone, self reinforced polyphenylene, polyolefin, polyester, polyimide, polyamide, and polyacrylate.

13. The method of claim 10, comprising treating at least a portion of the polymeric bone contacting surface with hydroxyapatite.

14. The method of claim 10, wherein the first and second polymers are the same.

15. The method of claim 10, comprising providing a core in the mold prior to introducing the first polymer.

16. The method of claim 10, comprising introducing a pore forming agent into the first polymer.

17. The method of claim 10, comprising introducing a pore forming agent into the second polymer.

18. The method of claim 10, wherein one of the first polymer and the second polymer includes a pore forming agent selected from the group consisting of an expanding agent, a blowing agent, and a supercritical fluid.

19. The method of claim 10, wherein exposing the pores of the polymeric bone contacting surface includes removing a portion of the polymeric body.

20. The method of claim 19, wherein removing the portion of the polymeric body includes at least one of machining, grinding, sanding, and combinations thereof.

* * * * *